US010679750B2

(12) United States Patent
Astigarraga et al.

(10) Patent No.: US 10,679,750 B2
(45) Date of Patent: Jun. 9, 2020

(54) SYSTEM, METHOD, AND STORAGE MEDIUM TO GENERATE PREDICTIVE MEDICAL FEEDBACK

(71) Applicant: International Business Machines Corporation, Armonk, NY (US)

(72) Inventors: Tara Astigarraga, Fairport, NY (US); Christopher V. DeRobertis, Hopewell Junction, NY (US); Louie A. Dickens, Tucson, AZ (US); Jose R. Mosqueda Mejia, Puruandiro (MX); Daniel J. Winarski, Tucson, AZ (US)

(73) Assignee: International Business Machines Corporation, Armonk, NY (US)

( * ) Notice: Subject to any disclaimer, the term of this patent is extended or adjusted under 35 U.S.C. 154(b) by 616 days.

(21) Appl. No.: 15/232,364

(22) Filed: Aug. 9, 2016

(65) Prior Publication Data

US 2018/0046770 A1    Feb. 15, 2018

(51) Int. Cl.
| | | |
|---|---|---|
| G06F 15/18 | (2006.01) | |
| G16H 50/20 | (2018.01) | |
| G16H 20/60 | (2018.01) | |
| G16H 40/63 | (2018.01) | |
| G16H 10/60 | (2018.01) | |

(52) U.S. Cl.
CPC ............ *G16H 50/20* (2018.01); *G16H 10/60* (2018.01); *G16H 20/60* (2018.01); *G16H 40/63* (2018.01)

(58) Field of Classification Search
CPC ........ G16H 40/67; G16H 50/20; G16H 40/63; G09B 19/009; G06F 17/18; A61B 5/0205

USPC ..................................................... 706/15, 45
See application file for complete search history.

(56) References Cited

U.S. PATENT DOCUMENTS

| | | | |
|---|---|---|---|
| 7,970,633 B2 | 6/2011 | Bulat | |
| 8,015,145 B2 | 9/2011 | Liu et al. | |
| 8,690,578 B1 * | 4/2014 | Nusbaum | G09B 19/00 434/127 |
| 9,011,153 B2 | 4/2015 | Bennett et al. | |
| 9,148,483 B1 * | 9/2015 | Molettiere | H04L 67/22 |
| 2004/0116785 A1 | 6/2004 | Bulat | |
| 2006/0293572 A1 | 12/2006 | Bulat | |
| 2007/0016451 A1 | 1/2007 | Tilson | |
| 2010/0136508 A1 * | 6/2010 | Zekhtser | G09B 19/0092 434/127 |
| 2011/0301505 A1 | 12/2011 | Chen Wang et al. | |
| 2013/0307918 A1 | 11/2013 | Bulat | |
| 2014/0255882 A1 | 9/2014 | Hadad et al. | |
| 2014/0316220 A1 * | 10/2014 | Sheldon | A61B 5/0205 600/301 |
| 2014/0380218 A1 | 12/2014 | Johnnie | |

(Continued)

FOREIGN PATENT DOCUMENTS

| | | |
|---|---|---|
| WO | 2014/134375 A1 | 9/2014 |
| WO | 2014/178077 A2 | 11/2014 |

*Primary Examiner* — David R Vincent
(74) *Attorney, Agent, or Firm* — Kunzler Bean & Adamson (57) ABSTRACT

A system that includes one or more processors and one or more memories storing code that is executable by the one or more processors to: access a data log corresponding to a diet of a user over a predetermined period; determine a diet context for the user based at least in part on the data log; analyze the data log to determine a variance in the diet context; determine a potential medical issue in response to the variance; and generate predictive feedback for the user in response to the potential medical issue.

20 Claims, 6 Drawing Sheets

(56) References Cited

U.S. PATENT DOCUMENTS

| | | |
|---|---|---|
| 2015/0220624 A1 | 8/2015 | Bhatt et al. |
| 2015/0261928 A1 | 9/2015 | Refvik |
| 2015/0278622 A1 | 10/2015 | Fan et al. |
| 2015/0364057 A1 | 12/2015 | Catani et al. |
| 2016/0000323 A1 | 1/2016 | Myr |
| 2016/0071432 A1 | 3/2016 | Kurowski et al. |
| 2016/0225284 A1 | 8/2016 | Schoen et al. |
| 2017/0249445 A1* | 8/2017 | Devries ................. G16H 10/60 |

* cited by examiner

Diet Context 105

| Data Log 245 |
|---|
| Items Consumed 300 |
| Quantity 302 |
| Time Consumed 304 |
| Location of Consumption 306 |
| Nutritional Data 308 |
| Other Diet Data 309 |
| Wellness Indicator 310 |
| Time Assessed 312 |
| Appetite 314 |
| Mood 316 |
| Stress Level 318 |
| Other Wellness Indicators 319 |

| User Profile 250 |
|---|
| User Demographics 320 |
| Age 322 |
| Domicile 323 |
| Body size 324 |
| Gender 325 |
| Race 326 |
| Culture 327 |
| Relatives 328 |
| Other Demographics 329 |
| Eating Preferences 330 |
| Cuisine 332 |
| Schedule 334 |
| Other Preferences 336 |

Figure 3A

| Potential Medical Issue(s) 280 |
|---|
| Issue name 340 |
| Description 350 |
| Symptoms 352 |
| Prognosis 354 |
| Other descriptors 356 |
| Issue Type 360 |
| Eating Disorder 362 |
| Food Intolerance 364 |
| Food Allergy 366 |
| Disease 367 |
| Mental Illness 368 |
| Other Issue-types 369 |
| Contributory Factors 370 |
| Diet-related 372 |
| Demographic 374 |
| Location 376 |
| Public Health 377 |
| Other factors 378 |
| Diagnostic Test(s) 380 |

SYSTEM, METHOD, AND STORAGE MEDIUM TO GENERATE PREDICTIVE MEDICAL FEEDBACK

FIELD

The subject matter disclosed herein relates to computing systems, specifically, computer systems for generating predictive medical feedback.

BACKGROUND

Mobile computing devices may include applications to track a user's diet and related activities. Some applications allow a user to share information such as meal plans or nutritional information with other users. Some users carry mobile computing devices frequently which may enable them to conveniently input data regarding what they have eaten.

BRIEF SUMMARY

In one embodiment, a system is disclosed that includes one or more processors, and one or more memories storing code that is executable by the one or more processors to: access a data log corresponding to a diet of a user over a predetermined period; determine a diet context for the user based at least in part on the data log; analyze the data log to determine a variance in the diet context; determine a potential medical issue in response to the variance; and generate predictive feedback for the user in response to the potential medical issue.

In one embodiment, a method is disclosed that includes accessing, by processor, a data log corresponding to a diet of a user over a predetermined period; determining, by processor, a diet context for the user based at least in part on the data log; analyzing, by processor, the data log to determine a variance in the diet context; determining, by processor, a potential medical issue in response to the variance; and generating, by processor, predictive feedback for the user in response to the potential medical issue.

In one embodiment, a non-transitory computer-readable storage medium having instructions stored thereon is disclosed, that in response to execution, cause a system including one or more processors to: access a data log corresponding to a diet of a user over a predetermined period; determine a diet context for the user based at least in part on the data log; analyze the data log to determine a variance from the diet context; determine a potential medical issue in response to the variance; and generate predictive feedback for the user in response to the potential medical issue.

BRIEF DESCRIPTION OF THE DRAWINGS

In order that the advantages of the embodiments of the invention will be readily understood, a more particular description of the embodiments briefly described above will be rendered by reference to specific embodiments that are illustrated in the appended drawings. Understanding that these drawings depict only some embodiments, and are not therefore to be considered to be limiting of scope, the embodiments will be described and explained with additional specificity and detail through the use of the accompanying drawings, in which.

DETAILED DESCRIPTION

Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly predetermined otherwise. The terms "including," "comprising," "having," and variations thereof mean "including but not limited to" unless expressly predetermined otherwise. An enumerated listing of items does not imply that any or all of the items are mutually exclusive and/or mutually inclusive, unless expressly predetermined otherwise. The terms "a," "an," and "the" also refer to "one or more" unless expressly predetermined otherwise.

Furthermore, the described features, advantages, and characteristics of the embodiments may be combined in any suitable manner. One skilled in the relevant art will recognize that the embodiments may be practiced without one or more of the specific features or advantages of a particular embodiment. In other instances, additional features and advantages may be recognized in particular embodiments that may not be present in all embodiments.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk drive ("HDD"), a solid-state disk drive ("SDD"), a random access memory ("RAM"), a read-only memory ("ROM"), an erasable programmable read-only memory ("EPROM" or Flash memory), a static random access memory ("SRAM"), a portable compact disc read-only memory ("CD-ROM"), a digital versatile disk ("DVD"), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts predetermined in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act predetermined in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts predetermined in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the predetermined logical function(s). In some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved.

It will also be noted that each block of the block diagrams and/or flowchart illustration, and combinations of blocks in the block diagrams and/or flowchart illustration, can be implemented by special purpose hardware-based systems that perform the predetermined functions or acts or carry out combinations of special purpose hardware and computer instructions. Blocks or elements, labelled using singular descriptions may include multiple of the blocks of objects in some embodiments. Similarly, blocks, elements, and/or objects labelled using plural form descriptions do not necessarily include a plurality of blocks, elements, and/or objects in some embodiments. Descriptions of Figures may refer to elements described in previous Figures, like numbers referring to like elements.

Figure 1:
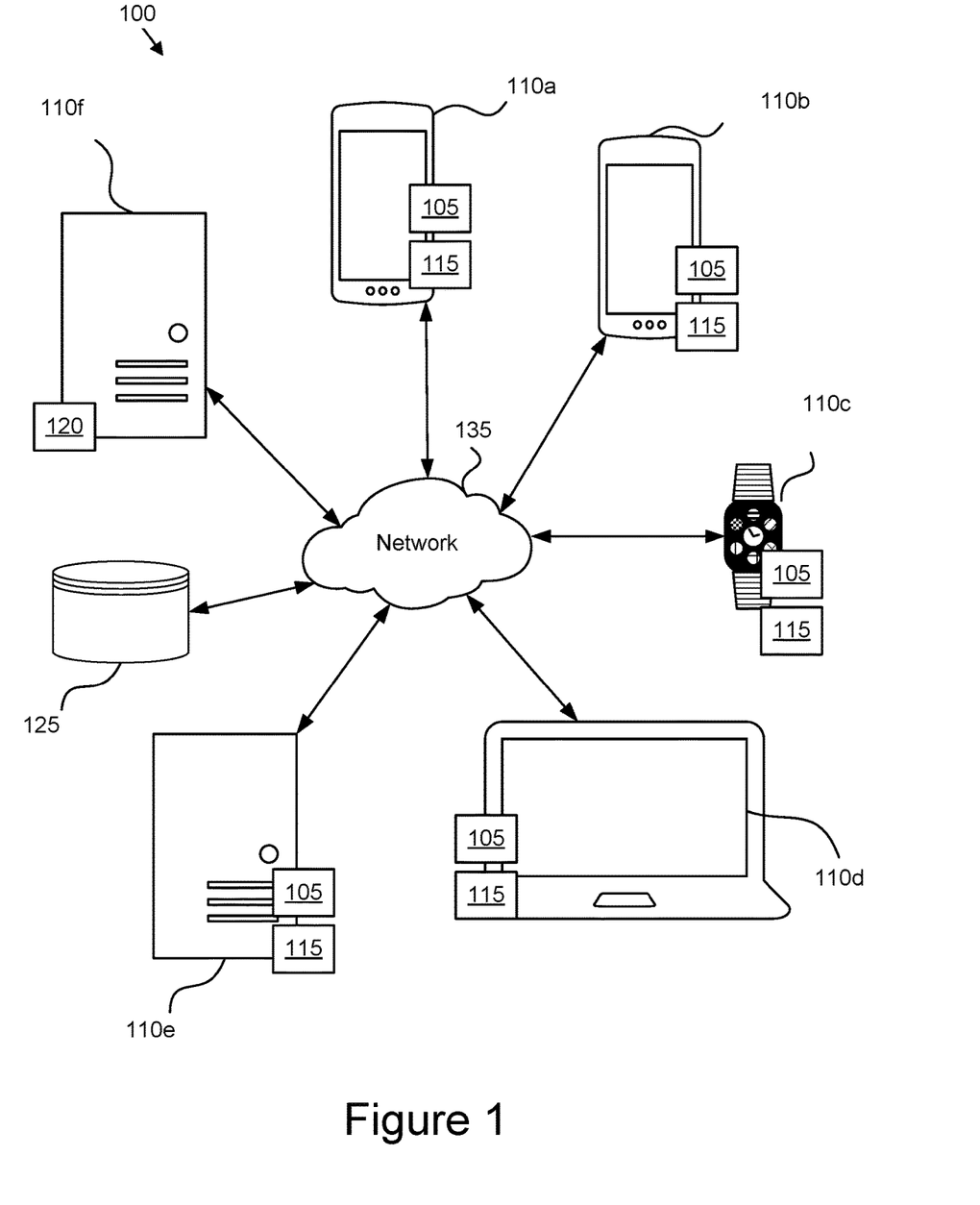
FIG. 1 is a schematic block diagram illustrating one embodiment of a system for generating predictive medical feedback based on cognitive analysis of diet data.

FIG. 1 is a schematic block diagram illustrating one embodiment of a system 100 for generating predictive medical feedback based on cognitive analysis of diet data. In one embodiment, the system 100 includes one or more computing devices 110, e.g. a first smart phone 110a, a second smart phone 110b, a wearable computing device 110c, a mobile laptop/notebook computer 110d, and/or other computing devices such as a server 110e. It may be understood that unless clearly indicated otherwise, a reference to a computing device 110 may refer to one or more of any computing device 110, e.g. 110a, 110b, 110c, 110d, 110e.

As used herein, the smart phone 110a, 110b may refer to a mobile phone that transmits and/or receives textual data. The wearable computing device 110c may be a smart watch, a fitness tracker, or any computing device that is attachable to, or wearable by, a user, and that is capable of accessing and/or displaying data regarding a user's diet. The mobile computing device 110d may be a laptop, a notebook, or tablet devices that do not have a physical keyboard. In some embodiments, the system 100 includes a data storage 125, e.g. cloud storage that is accessible via any other device on a network 135.

In some embodiments, the system 100 may include computing devices 110 having one or more applications that enable a user to capture and/or record data related to the user's diet. The data may form a portion of a user's diet context 105. The term diet, as used herein, may refer primarily to the items a person consumes and may include other information such as the type, quantity, and nutritional components of the items consumed. The term diet context 105, as used herein, may refer to data related to a person's diet that can be used to characterize the situation of a person, place, or object that is considered relevant to the interaction between a user and applications for computing devices that relate to the user's diet. In addition to data about the user's diet, the diet context 105 may include data about the user and the applications themselves. For example, the location or name of the user, demographic data about the user, account data about a user, the status of an application, or a relationship between two applications, and so forth. Examples of the types of data that may be included in a diet context 105 are depicted below with respect to FIG. 3A.

In an embodiment, the system 100 may include computing devices 110 that may include and/or communicate with a diet medical analyzer 115 for determining potential medical issues 280. The operation of the diet medical analyzer 115 for determining potential medical issues is described below in more detail with respect to FIGS. 2B and 3B. It may be understood that in some embodiments, the diet medical analyzer 115 may be included in one or more computing device 110. In other embodiments, the system 100 may be a distributed apparatus where, for example, a first portion of diet medical analyzer 115 may be included in a portable computing device 110, e.g. smart phone 110a, and a second portion of diet medical analyzer 115 may be included on the server 110e that is accessible by a computing device 110 through network 135, e.g. the Internet.

In one embodiment, each of the computing devices 110, e.g. 110a, 110b, 110c, 110d, and 110e, is depicted as including both at least a portion of a user's diet context 105 and at least a portion of diet medical analyzer 115. It will be understood that the system 100 may be fully operative in configurations in which one or more of the computing devices 110 does not include a portion of diet medical analyzer 115. For example, in some embodiments, computing device 110 may use a browser application to connect via network 135 with a diet medical analyzer 115 hosted on another computing device 110 such as server 110e.

In some embodiments, the system 100 further includes a meal planner 120. The meal planner 120 may also be included in a mobile computing device 110, e.g. 110a, 110b, 110c, 110d. In other embodiments at least a portion of meal planner 120 may be a meal planner 120 that is cloud-based, e.g. hosted on one or more servers 110f. One example of a meal planner 120 that is cloud-based is called Chef Watson® by IBM®. Chef Watson® uses cognitive computing to analyze textual sources of recipes and other meal related data to automatically generate meal plans based on user input. The computing devices 110 may include application programming interfaces (APIs) that communicate with the meal planner 120.

Figure 2A:
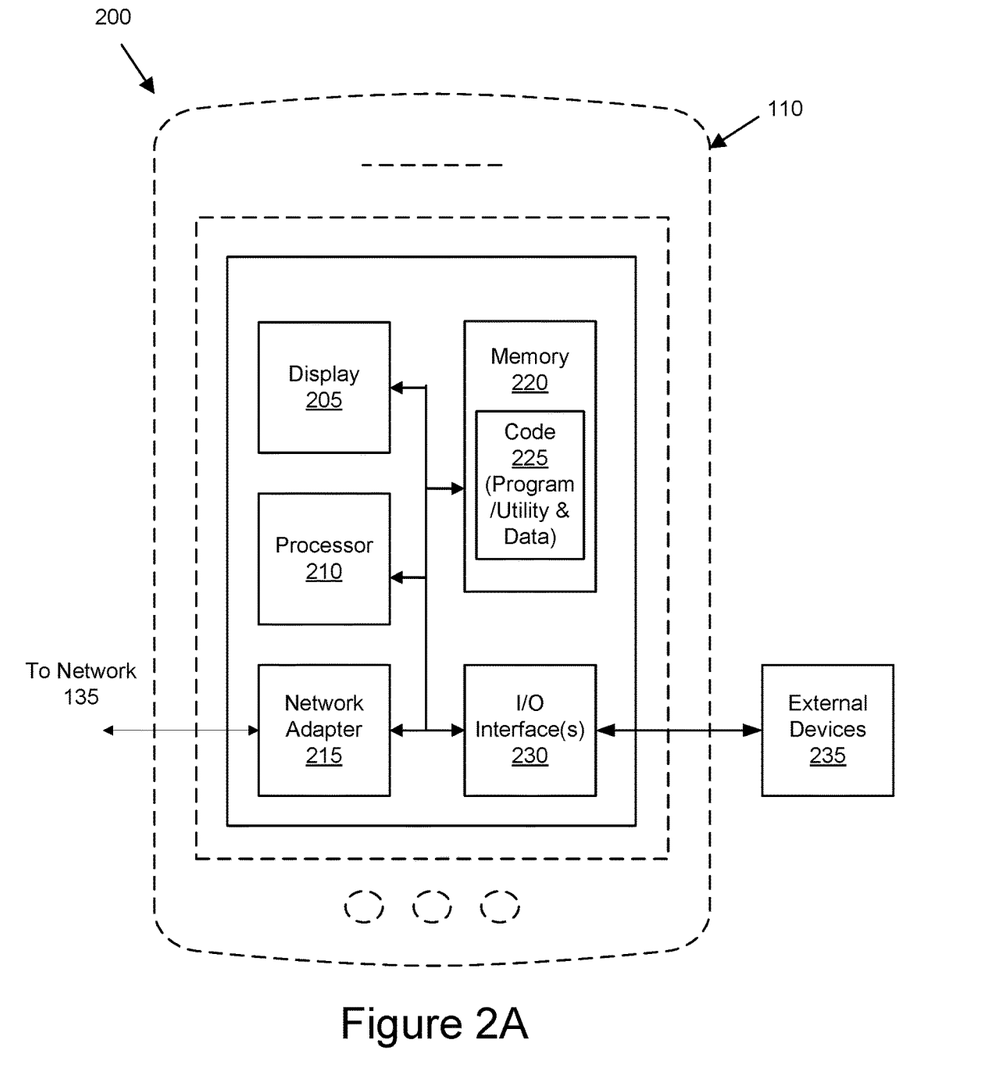
FIG. 2A is a schematic block diagram illustrating one embodiment of a system for generating predictive medical feedback based on cognitive analysis of diet data.
Figure 2B:
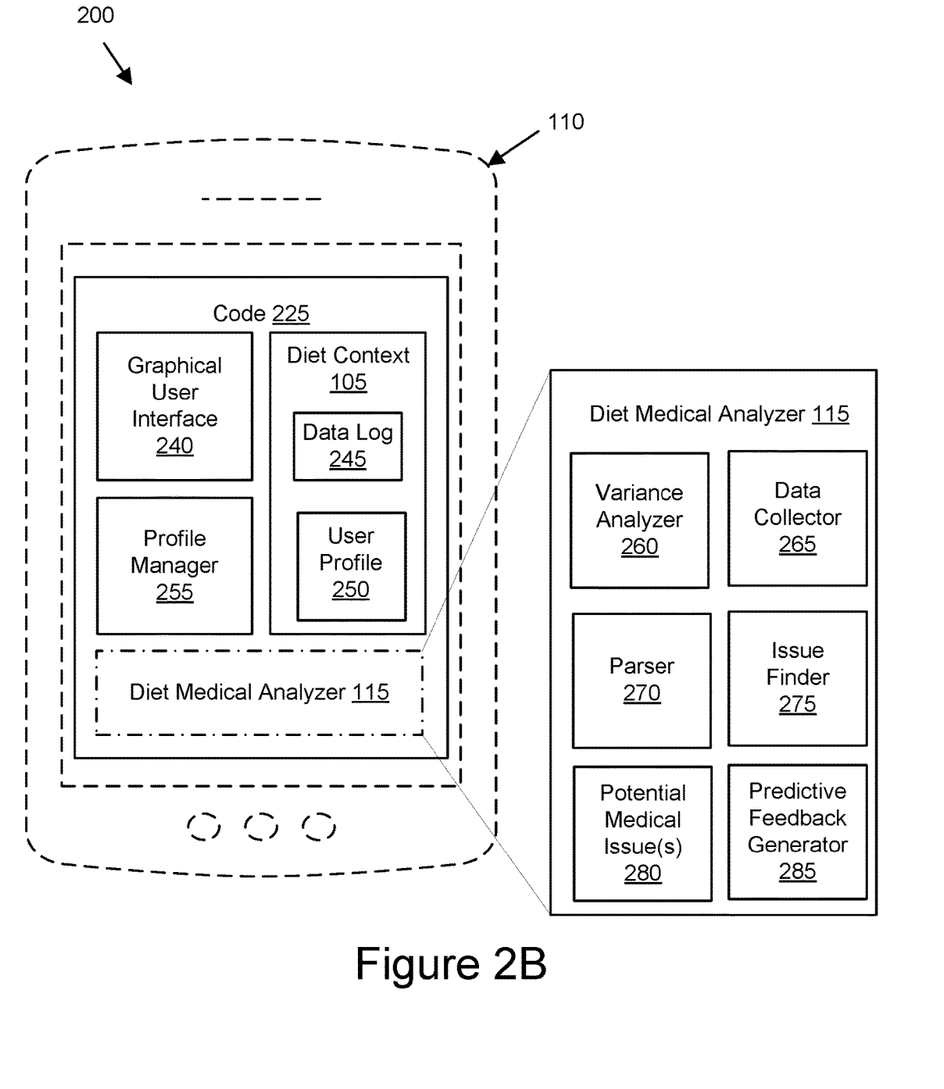
FIG. 2B is a schematic block diagram illustrating one embodiment of code for execution by the system of FIG. 2A.
Figure 3A:
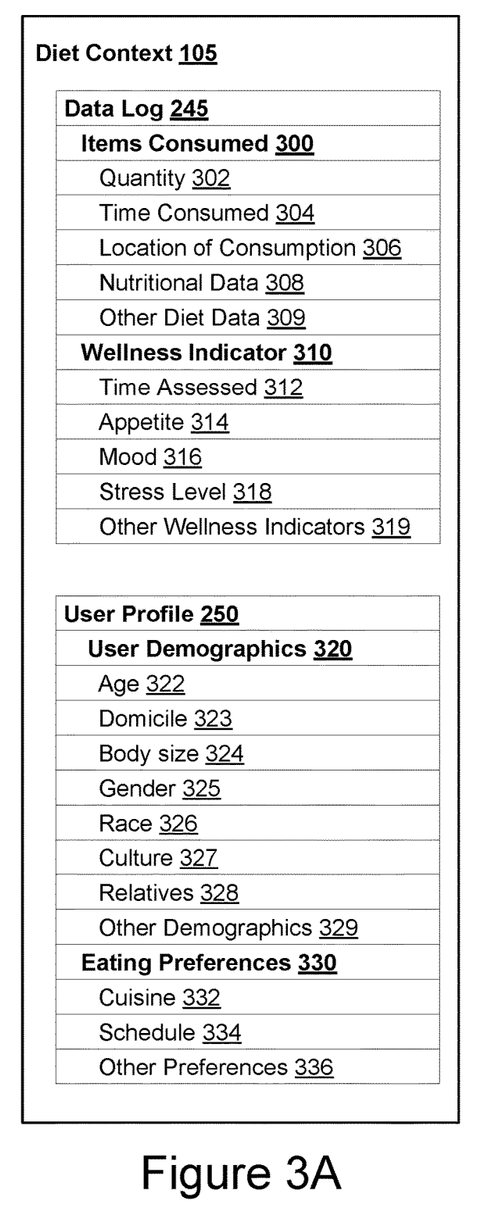
FIG. 3A is a schematic block diagram illustrating one embodiment of diet context data objects for cognitive analysis of diet data.
Figure 3B:
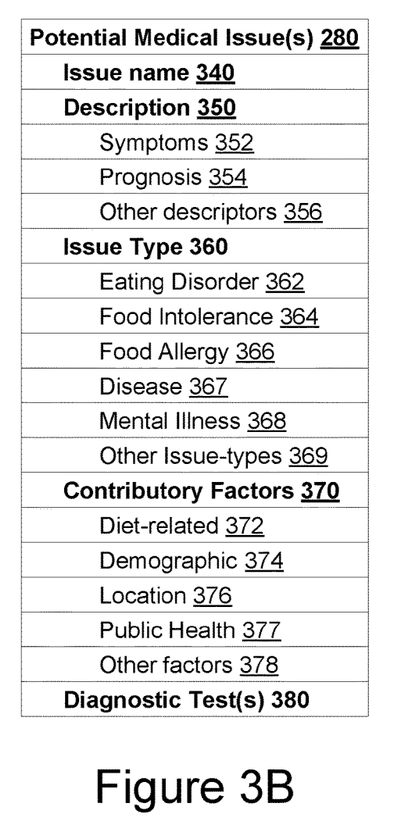
FIG. 3B is a schematic block diagram illustrating one embodiment of potential medical issue data objects.

FIGS. 2A and 2B are schematic block diagrams illustrating one embodiment of a system 200 for generating predictive medical feedback based on cognitive analysis of diet data. FIGS. 3A and 3B are schematic block diagrams illustrating one embodiment of diet context data objects for cognitive analysis of diet data and potential medical issue data objects respectively;

In one embodiment, illustrated in FIG. 2A, the system 200 includes a computing device 110 that has one or more processors 210 and one or more memories 220 storing code 225 executable by the one or more processors 210. The one or more memories 220 may be integrated memory including nonvolatile memory, static memory, and/or dynamic memory. The one or more memories 220 may also include removable memory such as for example, Secured Digital® (SD®) cards or microSD® cards.

In some embodiments, the computing device 110 includes a display 205 that displays texts and other graphical data. In some embodiments, display 205 includes one or more I/O interfaces 230 in the form of a touchscreen that allows a user to input text, e.g. with a finger or fingers or with a stylus. In some embodiments, the I/O interfaces 230 may connect to an external device 235 such as a storage device, an input device, or any other external device.

The computing device 110 may include other I/O interfaces 230. For example, computing device 110 may include an I/O interface such as a global positioning system (GPS) or any other location sensor that enables computing device 110 to determine its current location. In other embodiments, computing device 110 include a near field communication (NFC) as one of the I/O interfaces 230, that enables computing device 110 to communicate with another electronic device in close proximity. Other types of I/O interfaces 230 that enable the computing device 110 to communicate with external devices 235 may include Bluetooth® transceivers, wired microphone and headphone jacks, digital data transfer interfaces, and so forth. The system 200 may further include network adapter 215. The network adapter 215 may enable the computing device 110 to communicate with other computing devices 110, e.g. via network 135 which may be a wireless network in some embodiments.

The system 200 of FIG. 2B, in one embodiment, includes one or more processors 210 and one or more memories 220 that may be substantially similar to the one or more processors 210 and the one or more memories 220 described in FIG. 2A. The one or more memories 220 may store code 225 that is executable by the one or more processors 210 to access a data log 245 corresponding to a diet of a user over a predetermined period. The system 200 includes code 225 executable by one or more processors 210 to determine a diet context 105 for the user based at least in part on the data log 245. In some embodiments, system 200 includes a diet medical analyzer 115 that analyzes the data log 245 to determine a variance from the diet context.

The diet medical analyzer 115 further includes a data collector 265 which collects medical issue data from a variety of sources, for example, medical journals, news articles, websites, magazine articles, and so forth, to determine one or more potential medical issues 280 in response to the variance from the user's diet context 105. The diet medical analyzer 115 may include a parser 270 that parses the data collected by the data collector 265 to find words in the description of medical issues that relate to diet. The diet medical analyzer 115 may include an issue finder 275 that finds potential medical issues 280, for example, by comparing diet-related elements of the collected medical issue data with data from the diet context 105 of the user.

The diet medical analyzer 115 further includes a predictive feedback generator 285 that generates predictive feedback for the user in response to the potential medical issue 280. For example, in some cases, the text pertaining to the potential medical issues 280 may also include text relating to a diagnostic test 380 that may be able to detect a potential medical issue 280 prior to a user or physician being aware of the potential medical issue 280.

In some embodiments, the diet medical analyzer 115 may be included in code 225 stored on a memory 220 to be executed by a single processor in a single computing device 110. In some embodiments, computing device 110 is a mobile computing device such as smart phone 110a, 110b, wearable computing device 110c, or mobile laptop/notebook computer 110d. In other embodiments, a first portion of code 225 may be executed by a first processor 210 in a first computing device 110, e.g. smart phone 110a, and a second portion of code 225 may be executed on a second processor 210 in a second computing device 110, e.g. server 110e.

In some embodiments, the system 200 may operate primarily on a mobile computing device, e.g. 110a, 110b, 110c, and 110d. In other embodiments, the system 200 operates primarily on a computing device such as server 110e. The server 110e accesses the diet context 105 on the server 110e itself. For example, a user of a mobile device, e.g. 110a, 110b, 110c, and 110d may log into a website with a browser, or may open an "app" i.e. application, to enter diet context 105 including data log 245. In some embodiments, code 225 may include a graphical user interface 240 for user interaction with the system 200, e.g. for inputting and/or interacting with user data (e.g. data log 245, user profile 250, and/or displaying results (e.g. potential medical issues 280). In some embodiments code 225 includes a profile manager 255 for creating, modifying, deleting, and otherwise managing a user profile 250. In other embodiments, the diet context 105 including data log 245 and user profile 250 may be stored in memory 220 on a mobile computing device, e.g. 110a, 110b, 110c, and 110d. For example, the data log 245 may be included in a meal planning application, a calorie tracking application, a fitness application, or the like.

In still other embodiments, a first processor 210 within a mobile computing device e.g. 110a, 110b, 110c, and 110d captures at least a portion of the data log 245. A second processor 210, for example on a server 110e executes at least a portion of the code to determine the potential medical issue 280 in response to the variance. In some embodiments, a computing device 110, such as server 110e has significantly greater data collection and analysis resources than typical mobile computing devices 110a-110d. Powerful servers are often used in cognitive computing systems. As used herein, cognitive computing systems may refer generally to computing systems for interacting with humans naturally including analyzing unstructured and complex data, to generate hypotheses, reasoned arguments, and recommendations. IBM Watson® is one example of a powerful cognitive computing device that acts as a server to various applications that require data collection and analysis of large quantities of unstructured data, including textual data. Thus, in some preferred embodiments, diet medical analyzer 115 may be executed on a server 110e that has significant data gathering and processing resources.

As depicted in FIG. 3A, the data log 245 may include data objects such as items consumed 300 by a user over a predetermined period. The data log 245 may further include the quantity 302 of the items consumed 300 and the time consumed 304, meaning the time at which the items consumed 300 were consumed. Thus, the data log 245 captures data that may be used to determine eating patterns over a predetermined period of time. The data log 245 may further include data about the location of consumption 306 of the items consumed 300 or nutritional data 308, and or other diet data 309 related to the items consumed 300.

Referring in more detail to FIG. 3A, in some embodiments, the data log 245 may include other data objects related to items consumed 300. For example, nutritional data 308 or other diet data 309 may be available within data log 245 because a user has input the nutritional data 308 or the other diet data 309. Nutritional data 308 or the other diet data 309 may also be accessed from another source, using the names of the items consumed 300 and the quantity 302 to look up nutritional data 308.

In some embodiments, the data log 245 includes a wellness indicator 310. In other embodiments, the system 200 may operate effectively without the need for wellness indicator 310. As used herein, wellness generally may refer to a user's subjective perceptions or feelings that may be related to his or her diet. In some embodiments, the wellness indicator 310 may include data objects such as the time assessed 312, meaning the time at which the user assessed his or her wellness. The wellness indicator with 310 may also include an appetite 314 data object where the user records, for example, feeling full, or hungry. The wellness indicator may also include a mood indicator 316 or a stress level 318 or any other wellness indicator 319. In other embodiments, the wellness indicator 310 may be an objective measurement such as blood pressure, body temperature, redness, and so forth.

These wellness indicators may not be recognized as symptoms by a user, or by a physician. However, they may be useful in providing additional context for the dietary records related to items consumed 300. Similarly, the location of consumption 306 of the items consumed 300 may be recorded generally automatically, for example by recording a GPS location at the time the data log 245 was updated with items consumed 300. In some embodiments, the location of consumption 306 may be a relevant part of the diet context 105 if the variance is determined in the data log 245.

For example, a user may have eaten at a particular location of consumption 306 without perceiving any impact on his or her diet context 105, e.g. his or her eating patterns. Later in response to the determined variance in the user's diet context 105, the issue finder 275 may access the data object named location of consumption 306 and find data sources indicating that items, like the items consumed 300 at a particular location of consumption 306 may present potential medical issues 280. Additional examples are provided below.

In some embodiments, the diet context 105 also includes a user profile 250. User profile 250 may include user demographics 320 such as age 322, domicile 323, gender 325, race 326, culture 327, relatives 328, and/or other demographics 329. The user demographics 320 may be readily available from data already stored digitally, for example in a user account, or accessible by a data collector 265 that collects demographic data for a particular user from online sources, such as the user's social media accounts or genealogical databases for which the user has granted the system 200 access.

In some embodiments, the diet context 105 includes a user profile 250 that includes eating preferences 330 for a user. Eating preferences 330 for a user may include, for example a preferred cuisine 332, such as Chinese food, Italian food, or Cajun food. Eating preferences 330 may also include preferences regarding eating schedule 334. For example, a user may prefer to skip breakfast or a user may prefer to eat meals that take less than 20 minutes to prepare. In some embodiments, the eating preferences 330 may include other preferences 336. Thus, the diet context 105 which may include a data log 245 and a user profile 250 is a source of relevant data that may be used to analyze a particular user's diet and variances in a user's diet context 105.

Referring again to FIG. 2B, in some embodiments, the diet medical analyzer 115 includes a variance analyzer 260. The variance analyzer 260 may be implemented, for example, as software that is executed by a general purpose processor or may be implemented by programmable circuitry or as a combination of hardware and software. A variance analyzer 260 as depicted in FIG. 2B analyzes the data log 245 to determine a variance in the diet context 105. For example, a user may record a data log 245 that shows a regular pattern of eating dairy foods or spicy foods during the first portion of the predetermined period. Later, at a second portion of the predetermined period a user may log a pattern of eating a lesser quantity 302 of dairy foods or spicy foods.

Some variance in diet context 105 may be imperceptible to a user acting without the system 200, or the user may be unaware of the degree of variance. The variance analyzer 260 may include a predetermined threshold to determine whether a meaningful variance exists. In some embodiments, predetermined threshold may be predetermined by the user. In other embodiments the system may import a predetermined threshold from a user or from published data. In some embodiments, the predetermined threshold may be a composite threshold formed by a mathematical expression of a plurality of variables.

The variance analyzer 260 determines the variance in the diet context 105, e.g. a decrease in the quantity 302 of dairy items or spicy items consumed 300. Although a user may be unaware of any potential medical issues associated with the variance in diet from his or her typical diet context 105, the variance may in fact be useful in determining potential medical issues 280. Some examples of potential medical issues 280 are illustrated in FIG. 3B. For example, lactose intolerance is a potential medical issue 280 of a particular issue type 360, e.g. food intolerance 364.

In some embodiments, the variance analyzer 260 determines different types of variances in the diet context 105 of a particular user. In some embodiments, the term variance may refer to a statistical variance expression such as $Z=(X-\text{Average})/(\text{Standard Deviation})$ where $Z$ is the standardized normal variate and $X$ is the diet variable (e.g. quantity 302 in a predetermined period). If $Z=0$, then the measurement $X$ (of calories, grams of protein, carbohydrates, etc.) is equal to the average. If $Z=+1$, then the measurement $X$ is one standard deviation above the average. If $Z=+2$, then the measurement $X$ is two standard deviations above the average. If $Z=-1$, then the measurement $X$ is one standard deviation below the average. If $Z=-2$, then the measurement $X$ is two standard deviations below the average, and so forth. If $X$ represents something critical, such as carbohydrate intake by a user with diabetes, then a $Z$ value of $+1$ or $-1$ could trigger social media alerts to the user and friends. If the value of $Z$ of $+2$ or $-2$ could trigger alarms to medical personnel.

In some embodiments, the thresholds Zmax and Zmin need not be equal in value, as they were (for simplicity) in the above paragraph. The thresholds may vary for different portions of one's diet. For example, the variance analyzer may use a $Z$ thresholds of $+0.5$ or $-0.5$ instead of $+1$ and $-1$ (for Zmax and Zmin) when tighter tolerances are needed on critical items. Thus $Z$ (as defined above) is a very simple way of representing a normalized variance.

Figure 5:
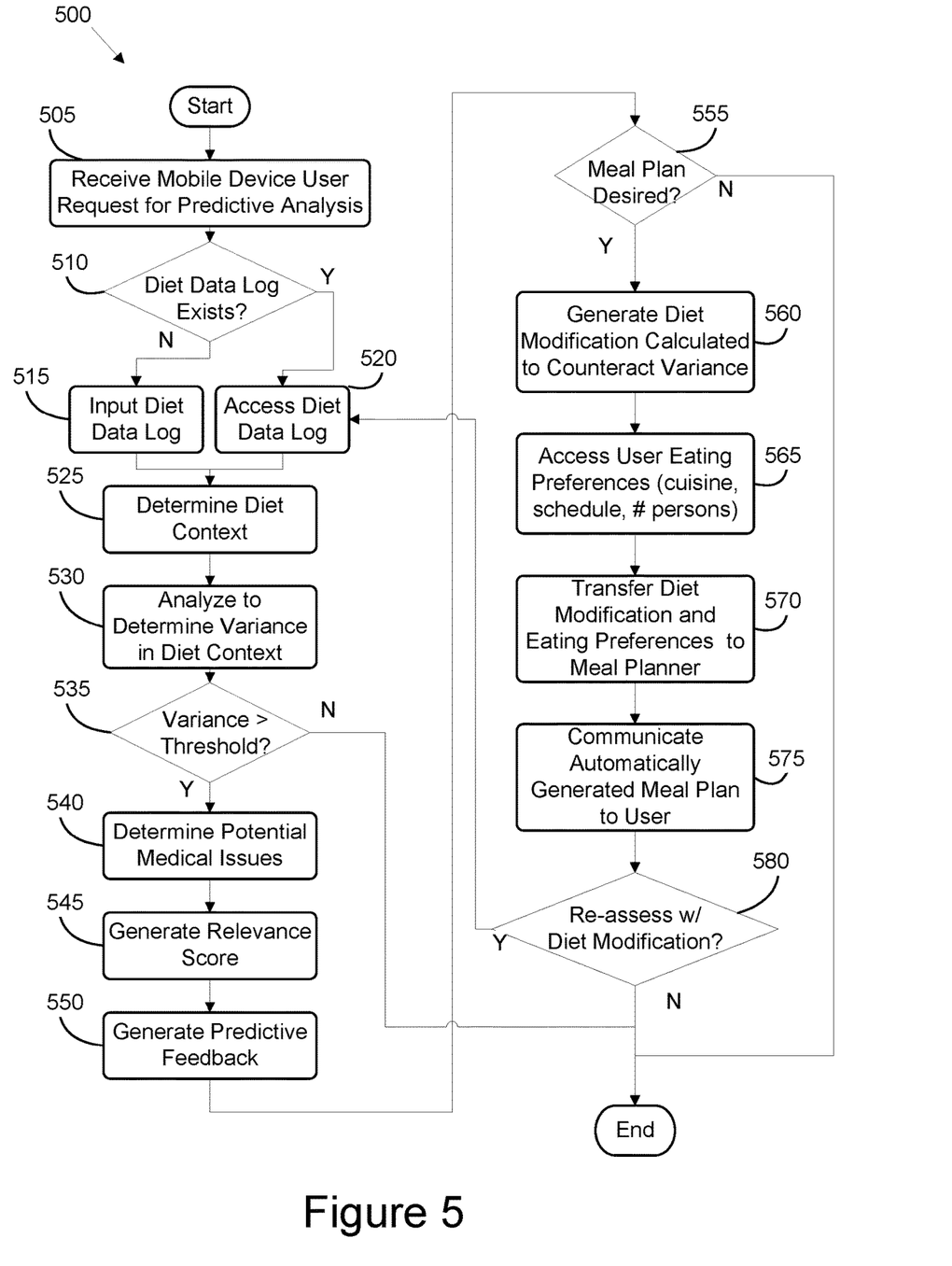
FIG. 5 is a flow chart diagram illustrating another embodiment of a method for generating predictive medical feedback based on cognitive analysis of diet data.

For example, the quantity 302 of items consumed 300 may be $X$ and a running average is subtracted from $X$, which is then divided by the Standard Deviation (assuming a Gaussian Distribution on the variance). When $Z$ exceeds a threshold (either too high or too low), that could trigger step 535. For example, if a user's intake of carbohydrates in a portion of the data log 245 is significantly higher or lower than a reference level (e.g. a prior level or a level of another person or group of persons) the method 500 may generate 550 predictive feedback regarding potential medical issues 280.

Variance may also be used in the broader sense to refer to a change or a difference. The variance from the diet context 105 may be a variance in the user's diet between a first portion of the predetermined period and a second portion of the predetermined period. In other words, a change in diet over time. In other embodiments, a variance may be between the user's diet and a third party's diet. For example, if a user's profile includes information about a third-party's diet (e.g., relative 328, a family member, or someone living in the same household) that includes items consumed 300 in the same location of consumption 306 as the user and the type of items consumed 300 by the user varies from the type of items consumed by the third party.

Determining this variance may be useful in determining potential medical issues 280 because the sources of the potential medical issues 280 may refer to items consumed 300 without referring to variance in diet, or may refer to deficiencies or excesses in a type of food item or nutrient. In some embodiments, the third-party may be a user of the system, e.g. the systems 100, 200. In other embodiments, the user may enter data relating to the third-party's diet into the systems 100, 200 for comparison against the user's own diet. Likewise, other diet context 105 data objects for the third-party may be entered into the systems 100, 200, either by the third-party or by the user.

A third type of variance from a diet context 105 of a user may include a variance between the user's diet and published diet standards for a demographic group to which the user belongs. For example, a user may have a particular age 322, and a particular body size 324. The body size 324 may include, for example, weight, height, and/or other measurements such as waistline size. The variance analyzer 260 may compare the data log 245 of the user with published dietary standards or ranges for people of a particular demographic group, e.g. a particular age range, a particular weight range, particular height range, and so forth. Thus, the variance analyzer 260 may determine a variance in the diet context of a user over time, a variance between a user's diet and a third party's diet, and/or a variance between the user's diet and published diet ranges for a demographic group to which the user belongs.

FIG. 3B is a schematic block diagram illustrating one embodiment of potential medical issue data objects. In some embodiments, each potential medical issue 280 may include an issue name 340 or equivalent identifier. Potential medical issues 280 may further include a description 350 that may include symptoms 352, prognosis 354, and other descriptors 356. After the data collector 265 accesses sources of potential medical issues, for example journals, magazines, websites, databases, and so forth, the parser 270 parses the text of the sources, and the issue finder 275 finds potential medical issues 280 which include text that corresponds to text within the user's diet context 105.

In some embodiments, the issue finder 275 searches for text in the description 350 data objects of the potential medical issues 280 that relate to variances in diet. For example, the phrases "loss of appetite", "craving", "lack of" or "due to an excess" of a particular nutrient, within text related to a potential medical issue may indicate that the issue is related to a variance in a user's diet context.

In some embodiments, the issue finder 275 searches for text in the potential medical issues 280 that relate to an issue type 360. The issue type 360 may include eating disorders 362, food intolerances 364, food allergies 366, diseases 367, mental illnesses 368, and/or other issue types 369, e.g. seasonal affective disorder, depression, job-related stress, post-traumatic stress disorder, etc. The issue type 360 may be useful to compare with the wellness indicators 310 and the diet context 105. The issue type 360 may further be useful in finding diagnostic tests 380 which the system 200 may include in generating predictive feedback for the user. Thus, the user may be made aware of diagnostic tests 380 that may predictively detect or confirm a particular potential medical issue 280 before the user is aware and/or before it becomes a more serious issue.

In some embodiments, the issue finder 275 searches for text in the potential medical issues that relate to a contributory factor 370. Diet-related factors 372 may be contributory factors 370 of primary interest. Other contributory factors such as demographic factors 374 may be useful to determine the relevance of a particular potential medical issue 282 a change in the diet context 105 of a particular user.

In some embodiments, a data object such as a location 376 may be a contributory factor to a potential medical issue 280 that is diet-related. The issue finder 275 may find that a particular type of cuisine eaten in a particular area is associated with potential medical issues 280. For example, there may be a custom in some location 376 of preparing food in a way that may contribute to potential medical issues such as by under cooking meats.

Additionally, the issue finder 275 may search for data objects such as public health factors 377. For example, particular menu items from particular restaurants at a particular location may have resulted in illnesses due to pathogens and/or toxins which are not immediately detectable by the consumer of those menu items, but after some period of time some consumers begin to experience medical issues. In some embodiments, the issue finder 275 searches for other factors 378 that may correspond to a variance in diet (e.g. physical activity, metabolism, hormones, temperature, palatability, boredom social influences, and so forth).

In some embodiments, the data collector 265 gathers vast amount of data from hundreds of news sources of which the user may be unaware. By determining a variance in an eating pattern of a user (e.g., a diet context item such as location of consumption 306 which is unusual for the particular user), the predictive feedback generator 285 of the diet medical analyzer 115 may generate predictive feedback that alerts the user to a potential medical issue related to the location of consumption 306. The location of consumption 306 may be a location where the items consumed 300 were consumed.

Accordingly, the embodiments of the system 200 may improve the function of the computing devices 110 that implement code 225 by enabling them to detect and determine potential medical issues related to the variance in diet context of which a user may be completely unaware. Moreover, the system 200 does not necessarily rely on the results of a diagnostic medical test whereby a user who is ill seeks to retrospectively examine potential causes of the illness. Rather, the system 200 determines potential medical issues 280 based on variances in the diet context 105.

Figure 4:
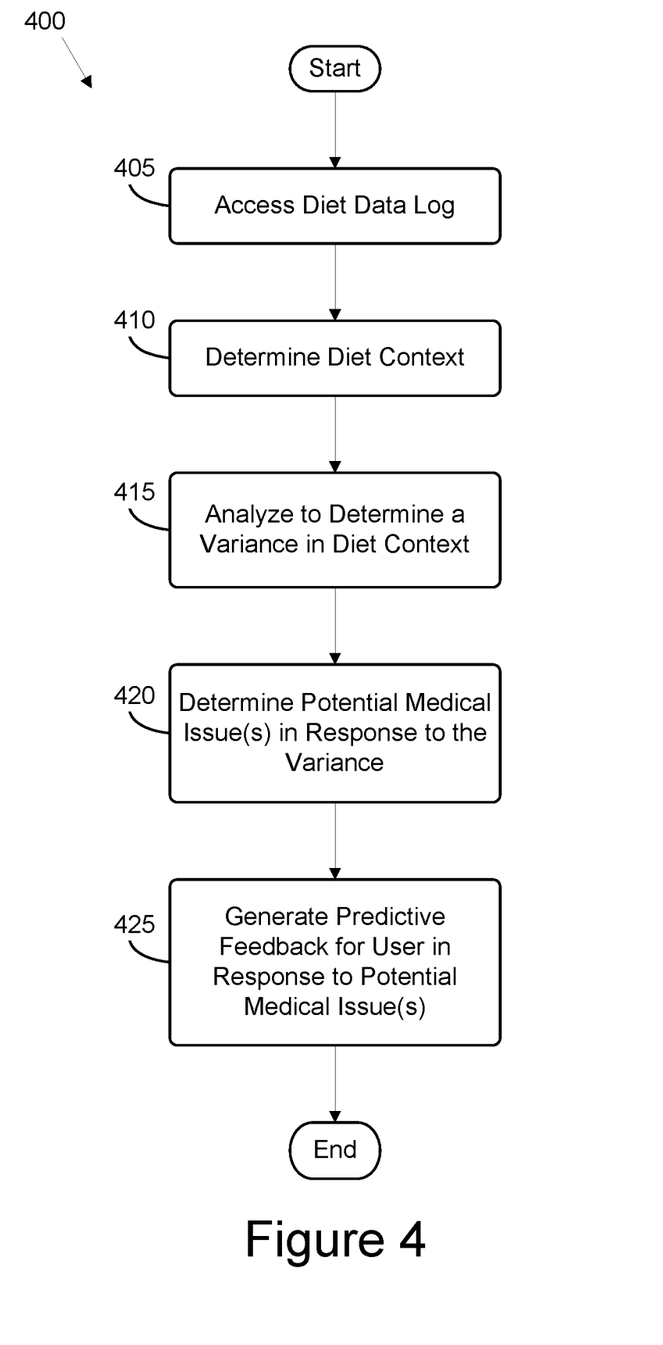
FIG. 4 is a flow chart diagram illustrating one embodiment of a method for generating predictive medical feedback based on cognitive analysis of diet data.

FIG. 4 is a flow chart diagram illustrating one embodiment of a method for generating predictive medical feedback based on cognitive analysis of diet data. In one embodiment, the method 400 includes accessing 405 a data log 245 corresponding to a diet of the user over predetermined period. In some embodiments, the method 400 is implemented on the server 110e and the data log 245 may be stored on the server 110e, stored on a mobile computing device e.g. 110a, 110b, 110c, and 110d, and accessed by the server 110e. In other embodiments the method 400 is implemented on a mobile computing device e.g. 110a, 110b, 110c, and 110d, and the data log 245 is stored on the same mobile computing device.

The method 400 includes determining 410 a diet context 105 for the user, based at least in part on the data log 245. The method 400 includes analyzing 415 the data log 245 to determine a variance from the diet context 105. In some embodiments, the analyzing 415 may be implemented by a diet medical analyzer 115 that includes a variance analyzer 260 as described above. The method 400 further includes determining 420 a potential medical issue 280 in response to the variance. In some embodiments, the determining 420 a potential medical issue 280 may be accomplished by a diet medical analyzer 115 that includes a data collector 265 that collects data about potential medical issues 280 and parses the data using parser 270.

The diet medical analyzer 115 may further include an issue finder 275 that analyzes the parsed data collected and compares textual data objects within the collected data with data objects in the diet context 105 of the user. The method 400 further includes 425 generating predictive feedback for the user in response to the potential medical issue 280. In some embodiments, the predictive feedback for the user may include one or more diagnostic tests 380 for further determining whether the potential medical issue 280 is relevant to the user.

As described above, one or more parts of method 400 may be implemented on a first processor of a system such as the system 200, while other parts of method 400 may be implemented in a separate part of the system 200 on a second processor. For example, in some embodiments, assessing the data log 245 and determining a diet context 105, may be done on a mobile computing device 110, such as smart phone 110a. The analyzing the data log 245 to determine a variance and determining the potential medical issue 280 in response the variance and generating predictive feedback for the user may be done by a second processor on a server 110e.

FIG. 5 is a flow chart diagram illustrating another embodiment of a method for generating predictive medical feedback based on cognitive analysis of diet data. In one embodiment, the method 500 includes receiving 505 a mobile device use or request for predictive analysis of potential medical issues 280 based on the user's diet. In some embodiments, the method 500 further queries 510 whether a data log 245 exists. If yes, the method 500 accesses 520 the data log 245. If no, the method 500 includes inputting 515 the data log 245. For example, by asking the user questions about items consumed 300.

In some embodiments, the data log 245 further includes a wellness indicator 310 provided by the user for the predetermined period. The method 500 includes determining 525 a diet context 105 for the user. The time period included in the data log 245 may be as short as a matter of days or maybe as long as many years depending on the period predetermined by the user or by a third-party that implements the method 500.

The method 500 further includes analyzing the data log 245 to determine a variance in the diet context 105 of the user. The variance may be a variance in the user's own diet over time, a variance between the user's diet and a third-party's diet, or a variance between a user's diet and published diet standards for demographic group to which the user belongs. In some embodiments, the method 500 checks 535 whether the variance is greater than a predetermined threshold. If not, then the method 500 ends. If yes, then the method 500 further determines 540 potential medical issues 280 related to the variance in the diet context 105 of the user. In some embodiments, the method 500 further generates 545 a relevance score. The relevance score may be used by method 500 to sort the potential medical issues 280 so that the more relevant potential medical issues 280 are presented first, or otherwise highlighted to the user.

The method 500 may further include generating 550 predictive feedback for the user in response to potential medical issues 280 determined in response to the variance in the user's diet context 105. In some embodiments, the predictive feedback may include one or more diagnostic tests 380 to further assess whether the user is likely to develop the potential medical issue 280. In some embodiments, the generating predictive feedback 550 may further includes generating predictive feedback message about potential medical issues 280 caused by the variation for communicating to persons whom the user has authorized to receive such messages. In some embodiments the predictive feedback may be tweeted, snapped, or otherwise broadcast on social media for immediate attention, to the user, and/or authorized doctors, nurses, friends, etc. This may allow an EpiPen® to be used in time to save someone's life.

In some embodiments, the method 500 checks 555 to see whether a meal plan for counteracting the variance is desired. For example, if the variance analyzer determines that a user's diet has significantly increased in consumption of carbohydrates, the method 500 may generate a diet modification for counteracting the variance, for example by planning meals that moderate consumption of items with a high-glycemic index or high glycemic load and that increase protein consumption to reduce inter-meal hunger. In addition to determining potential medical issues 280 and generating a diet modification for counteracting the variance, the method 500 may access 565 one or more eating preferences of the user.

For example, the user's preferred type of cuisine 332, the user's preferred schedule for eating and/or preparing meals, the number of persons for which the meal is to be planned, and so forth. Thus, the meal planner 120 may prepare a meal that addresses both the desired diet modification and the user's eating preferences. For example, a user may prefer to eat fruits and desire a diet modification that decreases glycemic load. Accordingly, the meal planner 120 may plan meals that includes more low glycemic load fruits such as strawberries, apricots, and/or grapefruit and that include fewer high glycemic load fruits such as bananas and grapes.

The method 500 may then transfer 570 diet data including, the data log 245, the eating preferences, and/or diet modification, to a meal planner 120 that automatically generates a meal plan taking into account the diet data. In any of the embodiments of the systems 100, 200, and/or methods 400, 500, the data that is transferred may be de-identified i.e. anonymized, before transferring so that a user's privacy is safeguarded.

The method 500 may then communicate 575 the automatically generated meal plan to the user. In some embodiments, the method 500 may query 580 whether the user wants to re-assess for potential medical issues after implementing the diet modification for a predetermined period of time. If yes, the method 500 repeats at least some of the steps, e.g. 520, 525, 530, 535, 540, 545, 550, 555, 560, 565, 570, 575, and/or 580 of the method 500. If not, the method 500 ends.

In some embodiments, the method 400 depicted in FIG. 4 and the method 500 depicted in FIG. 5 are carried out by a system 200 as illustrated in FIGS. 1, 2A, and/or 2B as described above. In other embodiments, the method is implemented by some other system or apparatus that differs from the system 200 as described, that performs the steps of method 400, and/or method 500 as described.

In some embodiments, the method 400 and/or the method 500 are implemented by a non-transitory computer readable storage medium having instructions stored, that when executed cars the system to access the data log 245 corresponding to a diet of a user over predetermined period of time. The instructions may further cause the system to determine a diet context 105 for the user based at least in part on the data log 245. Instructions may further cause the one or more processors 210 to analyze the data log 245 to determine a variance from the diet context 105.

The instructions may further cause the one or more processors 210 to determine a potential medical issue 280 in response to the variance. Instructions may further cause the one or more processors 210 to generate predictive feedback for the user in response the potential medical issue 280. It will be noted that instructions may cause the system comprising one or more processors 210 to access the data log 245 determine the diet context, analyze the data log 245 to determine a variance, determine the potential medical issue 280 in response to the variance, and generate predictive feedback, and may be in accordance the methods and systems described above.

As previously described, the diet context 105 may include data objects such as shown in FIG. 3A including items consumed 300, nutritional data 308, time consumed 304, location of consumption 306, user demographics 320, eating preferences 330, and combinations thereof. Likewise, the variance may be a variance in the user's diet between a first portion of the predetermined period and a second portion of the predetermined period, a variance between the user's diet and a third party's diet, and a variance between the user's diet and published standards for demographic group to which the user belongs. As previously described in some embodiments, the predictive feedback for the user may include a diagnostic test 380 to further assess whether the user is likely to develop the potential medical issues 280.

Thus, the systems 100, 200 improves the function of a computing device 110 by enabling it to detect potential medical issues based on variances in the user's diet context in ways that the user may be unable to perceive or analyze without the assistance of the system. The systems 100, 200 may further generate predictive feedback that may enable the user to obtain a diagnostic test which may otherwise be overlooked in the absence of a cognitive analysis of the user's diet. In some embodiments, the systems 100, 200 may generate and communicate to the user, a meal plan for counteracting potential medical issues 280 related to variance in the user's diet context 105.

The embodiments may be practiced in other specific forms. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A system comprising:
a mobile computing device comprising one or more processors;
a wireless network adapter configured to transfer diet data between the mobile communication device and a remote server comprising a cognitive computing system configured to retrieve, parse, and analyze unstructured online textual data and
one or more memories storing code that is executable by the one or more processors to:
transfer diet data over a network to data log corresponding to a diet of a user over a predetermined period;
transmit an authorization to the cognitive computing system to access an account of the user for a social media site that publishes unstructured text online;
wherein the cognitive computing system is further configured to
retrieve diet data from the data log by accessing the user account for the social media site;
parse unstructured text accessed from the social media account of the user to determine a diet context for the user based at least in part on the data log and on the parsed text from the social media site;
analyze the data log and the parsed text from the social media site to determine a variance in the diet context;
determine diet-context words corresponding to the variance;
transfer and parse medical issue data from unstructured text of a plurality of online sources based on the diet-context words;
determine a potential medical issue by determining which words parsed from the medical issue data correspond to the diet-context words of the set;
generate predictive feedback for the user in response to the potential medical issue; and
broadcast a message about the potential medical issue to the social media site.

2. The system of claim 1, wherein the mobile computing device captures at least a portion of the data log from a wearable device worn by the user.

3. The system of claim 1, wherein the diet context includes data objects selected from the group consisting of items consumed by the user, nutritional data corresponding to the items consumed, time consumed, location of consumption, demographic data, eating preferences, and combinations thereof and wherein determining the potential medical issue is based on data objects of the diet context corresponding to words in the unstructured text parsed by the cognitive computing system from the medical issue data that are indicative of public health issue related to items consumed by a third party at a corresponding location and a corresponding period of time to the items consumed, time consumed, and the location of consumption of the user.

4. The system of claim 3, wherein the variance in the diet context comprises a variance in the user's diet between a first portion of the predetermined period and a second portion of the predetermined period, and a variance between the user's diet and a third party's diet, wherein data for the third party's diet is de-identified to safeguard privacy of the third party before being transferred to the cognitive computing system.

5. The system of claim 4, wherein the variance in the diet context exceeds a predetermined threshold based on the medical issue data parsed from the plurality of online sources.

6. The system of claim 5, wherein the predictive feedback for the user further comprises a diagnostic test to further assess whether the user is likely to develop the potential medical issue.

7. The system of claim 4, wherein demographic data is stored in the online sources and is selected from social media data, genealogical data, and combinations thereof.

8. The system of claim 3, wherein the cognitive computing system is further configured to:
generate a diet modification calculated to counteract the variance;
accessing one or more eating preferences of the user;
transfer diet data for the user to a second cognitive computing system comprising a meal planner, the diet data selected from a group comprising the data log, the one or more eating preferences of the user, the diet modification, and combinations thereof, wherein the meal planner is configured to retrieve and parse unstructured text of recipes and other meal related data to generate a meal plan calculated to counteract the variance and satisfy the eating preferences of the user; and
transmit the generated meal plan to the user.

9. A method comprising:
transferring, to a remote server comprising a cognitive computing system configured to retrieve, parse, and analyze unstructured online textual data, a data log comprising diet data captured by a mobile computing device and corresponding to a diet of a user of the mobile computing device over a predetermined period;
transmitting an authorization to the cognitive computing system to access an account of the user for social media site that publishes unstructured online textual data;
retrieving diet data from the data log by accessing the user account for the social media site;
performing cognitive analysis, by processor, of unstructured text within the diet data accessed from the social media site to determine by processor, a diet context for the user based at least in part on the data log and on text retrieved and parsed from the social media site, wherein the text comprises subjective data posted by the user about feelings of the user;
analyzing, by processor, the data log to determine a variance in the diet context;
determining, by processor, a set of diet-context words corresponding to the variance;
transferring and parsing medical issue data from unstructured text of a plurality of publicly available online sources based on the set of diet-context words;
determining, by processor, a potential medical issue by determining which words parsed from the medical issue data correspond to the diet-context words; and
generating, by processor, predictive feedback for the user in response to the potential medical issue.

10. The method of claim 9, wherein at least a portion of the data log is captured by a wearable computing device worn by the user and wirelessly transmitted to the mobile computing device.

11. The method of claim 10, wherein the diet context includes data objects selected from the group consisting of items consumed by the user, nutritional data corresponding to the items consumed, time consumed, location, user demographics, eating preferences, and combinations thereof.

12. The method of claim 11, wherein the variance in the diet context comprises a variance in the user's diet between a first portion of the predetermined period and a second portion of the predetermined period, and a variance between the user's diet and published diet standards for a demographic group to which the user belongs.

13. The method of claim 12, further comprising sending a social media alert to friends of the user in response to determining that the variance in the diet context exceeds a predetermined threshold related to a potentially critical medical issue.

14. The method of claim 13, further comprising sending a social media alert based on the predictive feedback for the user wherein the social media alert includes a diagnostic test to further assess whether the user is likely to develop the potential medical issue.

15. The method of claim 14, wherein demographic data is stored in the online sources and is selected from social media data, genealogical data, and combinations thereof.

16. The method of claim 14, further comprising:
generating, by processor, a diet modification calculated to counteract the variance;
parsing, by processor, text related to one or more eating preferences of the user retrieved from;
transferring, by the processor, diet data for the user to a meal planner that performs cognitive analysis of text of the diet data, the diet data selected from a group comprising the data log, the one or more eating preferences, the diet modification, and combinations thereof, wherein the meal planner further performs retrieving, parsing, and performing cognitive analysis of textual sources of recipes to identify which of the recipes that satisfy the eating preferences of the user are also suitable for counteracting the variance; and
transmitting to the user, by processor, a meal plan generated by the meal planner based on the diet data.

17. A non-transitory computer-readable storage medium having instructions stored thereon that, in response to execution, cause a system comprising a cognitive computing system having one or more processors to:
parse text of a data log corresponding to a diet of a user over a predetermined period and comprising
a first portion comprising a digital record of items consumed by a user, wherein the digital record further comprises a location of consumption determined by a location sensor of a mobile computing device and a time consumed captured by a mobile computing device;
a second portion comprising a subjective wellness indicator captured by a touch screen of the mobile computing device in response to text being displayed on the touch screen;
a third portion comprising demographic data for the user stored in a social media site for which the system has been granted data retrieval access;
a fourth portion comprising an objective wellness indicator comprising a measurement of a physical state of the user;
determine a diet context for the user based at least in part on the data log;
analyze the data log to determine a variance from the diet context;
determine a potential medical issue in response to the variance; and
generate predictive feedback for the user in response to the potential medical issue.

18. The non-transitory computer-readable storage medium of claim 17, wherein the diet context comprises nutritional data corresponding to the items consumed, eating preferences, and combinations thereof.

19. The non-transitory computer-readable storage medium of claim 18, wherein the variance from the diet context comprises a variance in the user's diet between a first portion of the predetermined period and a second portion of the predetermined period, a variance between the user's diet and a third party's diet, and a variance between the user's diet and published diet standards for a demographic group to which the user belongs.

20. The non-transitory computer-readable storage medium of claim 19, wherein the predictive feedback for the user comprises a diagnostic test to further assess whether the user is likely to develop the potential medical issue.

* * * * *